United States Patent [19]

Greenlee

[11] 4,442,030

[45] Apr. 10, 1984

[54] PROCESS FOR PREPARING CARBOXYALKYL DIPEPTIDES

[75] Inventor: William J. Greenlee, Teaneck, N.J.

[73] Assignee: Merck & Co., Inc., Rahway, N.J.

[21] Appl. No.: 462,727

[22] Filed: Jan. 31, 1983

Related U.S. Application Data

[63] Continuation-in-part of Ser. No. 385,745, Jun. 7, 1982, abandoned.

[51] Int. Cl.$^3$ ............................................. C07C 103/52
[52] U.S. Cl. ............................................. 260/112.5 R
[58] Field of Search ................................. 260/112.5 R

[56] References Cited

PUBLICATIONS

Cromwell et al.; J.A.C.S., vol. 78, (1956), 4412–4416.

Primary Examiner—Delbert R. Phillips
Attorney, Agent, or Firm—Salvatore C. Mitri; Mario A. Monaco

[57] ABSTRACT

A process is disclosed for preparing carboxyalkyl dipeptides of the formula:

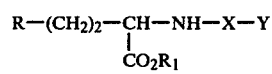

I

10 Claims, No Drawings

PROCESS FOR PREPARING CARBOXYALKYL DIPEPTIDES

BACKGROUND OF THE INVENTION

This is a continuation-in-part of application Ser. No. 385,745 filed June 7, 1982, now abandoned.

The preparation and pharmaceutical use of novel carboxyalkyl dipeptides as well as derivatives and analogs thereof have been disclosed in European Patent Application Ser. No. 12,401, which is incorporated herein by reference. The compounds disclosed in said European Patent Application are useful as converting enzyme inhibitors and as antihypertensive agents.

SUMMARY OF THE INVENTION

This invention is directed toward a process for preparing carboxyalkyl dipeptides of the kind disclosed in the aforementioned European Patent Application. Thus, the process of this invention is directed toward preparing carboxyalkyl dipeptides of the formula:

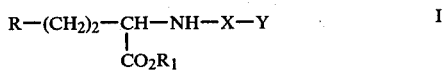

wherein
R is
  aryl (such a phenyl, naphthyl, or biphenyl);
  substituted aryl wherein the substituent can be loweralkyl, loweralkoxy, or halo;
  heteroaryl which can optionally include an O or N atom;
  substituted heteroaryl wherein the substituent(s) on the aryl and heteroaryl groups is (are) halo, dihalo, loweralkyl, hydroxy, loweralkoxy, acylamino, haloloweralkyl;
$R_1$ is loweralkyl of 1 to 4 carbon atoms;
X is
  alanine;
  glycine;
  isoleucine;
  leucine;
  lysine;
  phenylalanine;
  valine;
Y is
  alanine;
  glycine;
  isoleucine;
  leucine;
  lysine;
  phenylalanine;
  proline;
  valine; and,
the pharmaceutically acceptable salts thereof.
  Preferred are compounds of Formula I wherein:
  R is aryl or substituted aryl; and
  $R_1$, X and Y are as defined above.
  Still more preferred are compounds of Formula I wherein:
  R is phenyl;
  $R_1$ is ethyl; and,
  X and Y are as defined above.
  Most preferred are compounds of Formula I wherein:
  R is phenyl;
  $R_1$ is ethyl;
  X is alanine; and,
  Y is proline.

The preferred, more preferred, and most preferred compounds of Formula I also include the pharmaceutically acceptable salts thereof.

The loweralkyl groups, except where noted otherwise, represented by any of the variables include straight, branched, and unsaturated chain hydrocarbon radicals of $C_1$-$C_6$ such as, for example, methyl, ethyl, propyl, isopropyl, butyl, isobutyl, t-butyl, pentyl, isopentyl, hexyl, and the like. The aralkyl and heteroaralkyl groups represented by any of the variables have from 1–6 carbon atoms in the alkyl portion thereof and include, for example, benzyl, phenethyl, 3,3-diphenylpropyl, 3-indolylmethyl, and the like. Halo means chloro, bromo, iodo, or fluoro. Aryl where it appears in any of the radicals, except where noted, represents phenyl, naphthyl, or biphenyl. Heteroaryl includes, for example, indolyl, thienyl, imidazolyl, furyl, benzimidazolyl, pyridyl, quinolinyl, isoquinolinyl, and benzothienyl. Acylamino refers to lower alkanoylamino and aroylamino groups such as, for example, acetylamino, benzylamino, and the like.

The process of the invention is illustrated in the following Reaction Scheme wherein preferred reactants are shown to more clearly demonstrate the process of the invention.

REACTION SCHEME I

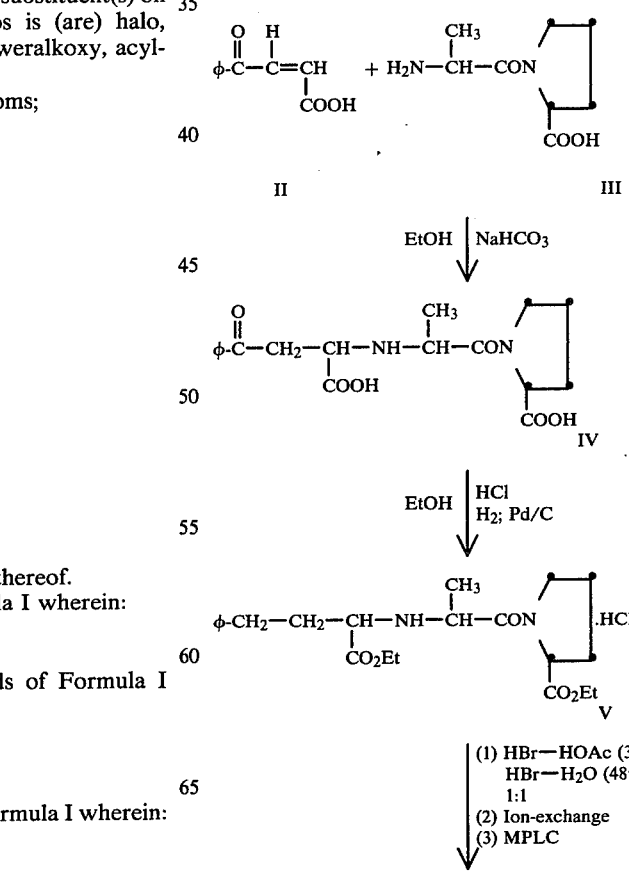

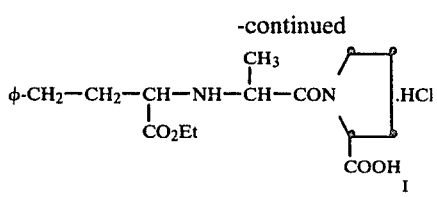

REACTION SCHEME II

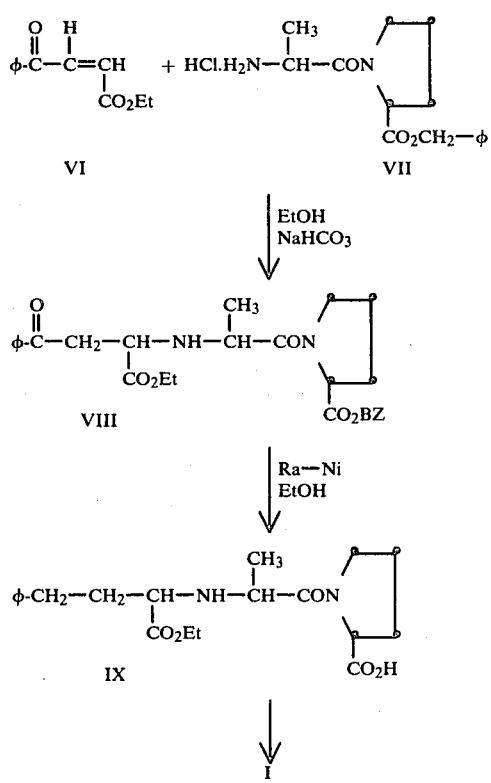

As shown Reaction Scheme I, 3-benzoylacrylic acid (II) is reacted with L-alanine-L-proline hemihydrate (III) in the presence of ethanol and sodium bicarbonate to obtain dicarboxy dipeptide IV. Dipeptide IV is then treated with ethanol and anhydrous hydrogen chloride and the resulting mixture subjected to hydrogenation in the presence of Pd/C catalyst to produce diester V as a mixture of diastereomers. This diastereomeric mixture V is then combined with hydrogen bromide-acetic acid and aqueous hydrobromic acid followed by ion-exchange chromatography and medium pressure liquid chromatography (MPLC) to afford monoester I as a mixture of diastereomers.

Further treatment of I with acetonitrile and maleic acid provides a crude maleate salt which can then be recrystallized to afford N-(1(S)-ethoxycarbonyl-3-phenylpropyl)-L-alanine-L-proline maleate salt.

In Reaction Scheme II, the ethyl β-benzoyl acrylate VI [prepared by the method of W. Koga, *Nippon Kagaku Zasshi*, 76, 1053–6 (1955)] is reacted with L-alanine-L-proline benzyl ester hydrochloride VII in the presence of ethanol and sodium bicarbonate to obtain protected dipeptide ester VIII. This dipeptide ester VIII is then treated with ethanol and Raney-Nickel catalyst [R. H. Mitchell, et. al, *Tetrahedron Lett*, 21, 2637 (1980)] to afford dipeptide ester IX. Treatment of IX with maleic acid provides I as the S,S,S-steroisomer maleate salt.

Thus, the process of the invention provides a simple, efficient and economical means to synthesize compounds of Formula I as the starting materials and basic reactants can either be readily prepared or are commercially available. In a preferred embodiment, diesters V or VIII can be prepared for shipment and transport and then converted to either the monoester salt or a compound of the Formula I.

The process of the invention will become more apparent and be better understood when considered together with the following Examples which are set forth as being further illustrative, and are not intended to be limitative, of the invention.

EXAMPLE 1

Ethyl N-(1-Carboethoxy-3-phenylpropyl)-L-alanyl-L-prolinate

To a solution of L-alanyl-L-proline hemihydrate (1.00 g; 5.12 mmol) and 3-benzoylacrylic acid (1.04 g; 5.91 mmol) in absolute ethanol (15 ml) there was added sodium bicarbonate (0.497 g; 5.91 mmol) and the mixture was stirred for 48 hours. After addition of ethanol (15 ml), the mixture was cooled (ice-bath) and anhydrous hydrogen chloride was passed in until the solution was saturated. Ethanol (5 ml) was added and the mixture was subjected to hydrogenation in the presence of 10% palladium on carbon 0.10 g) for 48 hours at 40 p.s.i. After removal of the catalyst by filtration and evaporation, the oily residue was taken up in $CH_2Cl_2$ and anhydrous ammonia was passed in until the solution was basic. The residue, after evaporation, was slurried with EtOAc and filtered. The residue, after evaporation, was subjected to column chromatography on silica gel with EtOAc as eluant, providing diester (1.1 g; 2.8 mmol; 54%) as a mixture (1:1) of diastereomers. TLC (silica gel; EtAc) Rf=0.50, 0.55.

NMR ($CDCl_3$): 1.1–1.3 (9H, m); 1.8–2.2 (6H, m); 2.6–2.8 (2H, m); 2.9–3.1 (1H, broad); 3.1–3.3 (1H, m); 3.4–3.6 (3H, m); 4.1–4.3 (4H, m); 4.4–4.6 (1H, m); 7.1–7.3 (5H, m).

IR ($CHCl_3$): 2960, 1730, 1640, 1430 cm$^{-1}$.

MS: m/e 404 (M+).

EXAMPLE 2

N-(1-Carboethxy-3-Phenylpropyl)-L-Alanyl-L-Proline or Its Maleate Salt.

The diester of Example 1 (0.508 g; 1.26 mmol) was combined with hydrogen bromide-saturated (32%) acetic acid (10 ml) and concentrated aqueous hydrobromic acid (2.5 ml), and the resulting solution was stirred vigorously for 48 hours. The solution was concentrated and then reconcentrated several times from $H_2O$. The oily residue was placed onto a column of DOWEX 50W-X4 (10 g). After an initial $H_2O$ wash of the resin, the product was eluted with 25:1 $H_2O$:pyr. Concentration left a colorless oil which TLC (silica gel; 100:20:3:0.5 $CHCl_3$:$CH_3OH$:$H_2O$:HOAc) shows to consist of monoester as a mixture (1:1) of diastereomers, Rf=0.65, 0.70, accompanied by a small amount of diacid, Rf=0.2. Medium pressure liquid chromatography on silica gel (E. Merck Lobar column, size A) in 100:20:3:0.5 $CHCl_3$:$CH_3OH$:$H_2O$:HOAc provided monoester (0.382 g; 1.02 mmol, 81%) as a mixture (1:1) of diastereomers. NMR ($D_2O$):1.30, 1.34 (3H, 2×t, J=7); 1.53, 1.58 (3H, 2×d, J=7); 1.8–2.0 (2H, m); 2.1–2.4 (4H, m); 2.7–3.0 (2H, m); 3.3–3.7 (2H, m); 3.8–4.2 (2H, m); 4.2–4.4 (3H, m); 7.3–7.5 (5H, m). IR (CHCl$_3$): 3500–2500, 2960, 1720, 1640, 1430 cm$^{-1}$. Ms (FAB): m/e 377 (M$^+$ +1). Separation of diastereomers was achieved by reverse-phase HPLC. Alternatively, separation can be achieved by treatment of a solution of the 1:1 mixture of isomers in acetonitrile solution with an acetonitrile solution containing a half-molar equivalent of maleic acid. After stirring for one hour at room temperature, the solid was collected and rinsed with acetonitrile and air-dried to yield maleate salt, by HPLC Ca. 96% pure. The crude maleate salt was recrystallized from acetonitrile to yield N-(1-(S)-ethoxycarbonyl-3-phenylpropyl)-L-alanyl-L-proline maleate salt, m.p. 148°–150° C., by HPLC ca. 99% pure, $[\alpha]_D^{25°} = -42°(CH_3OH)$.

EXAMPLE 3

N-(1-Carboxy-3-oxo-3-phenylpropyl)-L-alanyl-L-proline

To a solution of L-alanyl-L-proline hydrochloride (2.26 g; 10.2 mmol) and 3-benzoylacrylic acid (1.97 g; 11.2 mmol) in methanol (50 ml) there was added sodium bicarbonate (1.71 g; 20.3 mmol) and the mixture was stirred for 48 hours. After filtration and evaporation, the residue was purified on DOWEX 50W-XY using 10:1 H$_2$O:CH$_3$OH and then 50:1 H$_2$:pyr as eluants. Freeze drying of the H$_2$:pyr fractions gave the product as a mixture (1:1) of diastereomers (2.68 g; 7.40 mmol; 73%). MS: m/e 461 (bis trimethylsilyl M$^\oplus$-CO$_2$TMS). TLC (silica gel; 3:1:1:1 EtOAc, BuOH, HOAc, H$_2$O) Rf=0.35. NMR (D$_2$O): 1.08 (minor), 1.18 (minor), 1.26, 1.34 (3H, 4×d, J=7) (2 rotomers); 1.5–2.2 (4H, m); 2.1–3.8 (4H, m); 3.9–4.3 (3H, m); 7.307.8 (5H,m).

The diacid product of Example 3 can be obtained enriched in the diastereomer of (S,S,S) configuration by conducting the reaction in a two-phase reaction medium consisting of water and, for example, ether or dichloromethane or other solvent non-miscible with water. Accordingly, a solution of one molar equivalent of 3-benzoylacrylic acid in the organic solvent can be combined with an aqueous solution of L-alanyl-L-proline containing one molar equivalent of an inorganic base such as potassium bicarbonate. The reaction can be run with gentle stirring in the presence of a quaternary ammonium salt such as hexadecyltrimethylammonium, bromide or Triton B. Especially advantageous for obtaining optimum yields of the indicated diastereomer are chiral ammonium slats such as N,N-dimethylephedrinium bromide or N-dodecyl-N-methylephedrinium bromide. Also useful are crown ethers such as 18-crown-6 and dibenzo-18-crown-6.

Also useful for increasing the proportion of the above-mentioned diastereomer is a process in which a solution of 3-benzoylacrylic acid in an organic solvent such as, for example, benene, dichloromethane, or acetonitrile, can be added to L-alanyl-L-proline potassium salt, as prepared by treatment of the dipeptide with one molar equivalent of aqueous potassium hydroxide followed by freeze-drying. The reaction can be carried out under reflux in the presence of a quaternary ammonium salt such as dodecyltrimethylammonium bromide or, especially, N-dodecyl-N-methylephedrinium bromide, or a crown ether, for example 18-crown-6.

In the above-described processes, ethyl 3-benzoylacrylate can be substituted for 3-benzoylacrylic acid, leading to the ester, N-(1-carboethoxy-3-oxo-3-phenylpropyl)-L-alanyl-L-proline enriched in the diastereomer of (S,S,S) configuration.

In either case, the product can be isolated by concentration to dryness and purification as described above on DOWEX 50W-X4 acidic resin. Analysis of the diastereomeric composition can be carried out by reverse phase HPLC.

Alternatively, after concentration, the residue can be taken up in absolute ethanol, saturated with anhydrous hydrogen chloride, and treated further, as described in Example 1, to provide ethyl N-(1-carboethoxy-3-phenylpropyl)-L-alanyl-L-prolinate.

EXAMPLE 4

Alternative Process for N-(1-Carboethoxy-3-phenylpropyl)-L-alanyl-proline

L-Alanyl-L-proline benzyl ester hydrochloride (3.12 g; 10 mmol) can be combined with ethyl β-benzoylacrylate (2.04 g; 10 mmol), sodium bicarbonate (0.84 g; 10 mmol) and absolute ethanol (20 ml) and the mixture can then be stirred at room temperature for 24 hours. The mixture can then be filtered, and then water (2 ml) and W-7 Raney-Nickel catalyst (R. H. Mitchell, et al., *Tetrahedron Lett*, 21, 2637 (1980)) can be added and the mixture hydrogenated at 300 psi for 24 hours. After filtration to remove the catalyst and concentration to dryness, the residue can be taken up in acetonitrile and filtered. To the filtrate there can be added an acetonitrile solution containing a half-molar equivalent of maleic acid and, after stirring for one hour, the solid can be collected, rinsed with acetonitrile, and dried to yield the maleate salt.

N-(1-Carboethoxy-3-phenylpropyl)-L-alanyl-L-proline, prepared as described in Example 3 above, can also be treated with Raney-Nickel in ethanol-water, as described in Example 4 above, to obtain N-(1-carboethoxy-3-phenylpropyl)-L-alanyl-L-proline as the maleate salt.

What is claimed is:

1. A process for preparing carboxyalkyl dipeptides having the formula:

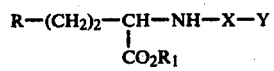

wherein
R is
  aryl;
  substituted aryl wherein the substituent can be loweralkyl, loweralkoxy, or halo;
  heteroaryl which can optionally include an O or N atom;
  substituted heteroaryl wherein the substituent(s) on the aryl and heteroaryl groups is (are) halo, dihalo, loweralkyl, hydroxy, loweralkoxy, acylamino, haloloweralkyl;
R$_1$ is loweralkyl of 1 to 4 carbon atoms;
X is
  alanine;
  glycine;
  isoleucine;
  leucine;
  lysine;
  phenylalanine;
  valine;
Y is alanine;
glycine;
isoleucine;
leucine;
lysine;
phenylalanine;
proline;
valine; and,
the pharmaceutically acceptable salts thereof; which process comprises:
reacting a compound having the formula:

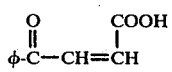

$$\phi\text{-}\overset{O}{\overset{\|}{C}}\text{-}CH=\overset{COOH}{\overset{|}{CH}} \qquad \text{II}$$

with a dipeptide to obtain a dicarboxy dipeptide; hydrogenating said dicarboxy dipeptide in an acidic medium in an alcohol solvent to afford, after concomittant esterification, a dicarboalkoxy dipeptide as a mixture of diasteromers; and, separating said diastereomeric mixture to produce said Formula I compounds.

2. The process of claim 1 wherein in said Formula I compound
R is aryl or substituted aryl; and,
$R_1$, X and Y are as defined in claim 1.

3. The process of claim 1 wherein in said Formula I compound
R is phenyl;
$R_1$ is ethyl; and,
X and Y are as defined in claim 1.

4. The process of claim 1 wherein in said Formula I compound
R is phenyl;
$R_1$ is ethyl;
X is alanine; and,
Y is proline.

5. The process of claim 1 wherein the treatment of said dicarboxy dipeptide is in the presence of Pd/C catalyst.

6. The process of claim 1 wherein the separation of said diastereomeric mixture is accomplished by ion-exchange chromatography and medium pressure liquid chromatography.

7. A process for preparing carboxyalkyl dipeptides having the formula:

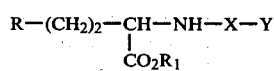

$$R\text{-}(CH_2)_2\text{-}\underset{\underset{CO_2R_1}{|}}{CH}\text{-}NH\text{-}X\text{-}Y \qquad \text{I}$$

wherein
R is
aryl;
substituted aryl wherein the substituent can be loweralkyl, loweralkoxy, or halo;
heteroaryl which can optionally include an O or N atom;
substituted heteroaryl wherein the substituent(s) on the aryl and heteroaryl groups is (are) halo, dihalo, loweralkyl, hydroxy, loweralkoxy, acylamino, haloloweralkyl;
$R_1$ is loweralkyl of 1 to 4 carbon atoms;
X is
alanine;
glycine;
isoleucine;
leucine;
lysine;
phenylalanine;
valine;
Y is
alanine;
glycine;
isoleucine;
leucine;
lysine;
phenylalanine;
proline;
valine; and,
the pharmaceutically acceptable salts thereof; which process comprises:
reacting a compound having the formula:

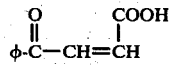

$$\phi\text{-}\overset{O}{\overset{\|}{C}}\text{-}CH=\overset{COOH}{\overset{|}{CH}} \qquad \text{II}$$

with a dipeptide benzyl ester hydrochloride to obtain a protected dipeptide ester; catalytically treating said ester to otain the diprotected dipeptide ester; and, treating said diprotected dipeptide ester with acetonitrile and maleic acid to obtain said Formula I compounds as S,S,S-steroisomer maleate salts.

8. The process of claim 7 wherein in said Formula I compound
R is aryl or substituted aryl; and,
$R_1$, X and Y are as defined in claim 1.

9. The process of claim 7 wherein in said Formula I compound
R is phenyl;
$R_1$ is ethyl; and,
X and Y are as defined in claim 1.

10. The process of claim 7 wherein in said Formula I compound
R is phenyl;
$R_1$ is ethyl;
X is alanine; and,
Y is proline.

* * * * *

UNITED STATES PATENT AND TRADEMARK OFFICE
CERTIFICATE OF CORRECTION

PATENT NO. : 4,442,030
DATED : April 10, 1984
INVENTOR(S) : W. J. Greenlee

It is certified that error appears in the above-identified patent and that said Letters Patent is hereby corrected as shown below:

Claim 1, Col. 7, lines 13-15, delete "$\phi\text{-}\overset{\overset{O}{\|}}{C}\text{-}CH\text{=}\overset{\overset{COOH}{|}}{C}H$" and insert, therefore, --$R\text{-}\overset{\overset{O}{\|}}{C}\text{-}CH\text{=}\overset{\overset{COOH}{|}}{C}H$--.

Claim 1, Col. 7, line 21, after "diastereomers;" insert --selectively hydrolyzing said dicarboalkoxy dipeptide to obtain a diastereomeric mixture of said Formula I compounds;--.

Claim 1, Col. 7, line 22, after "and" insert --optionally--.

Claim 1, Col. 7, line 23, after "compounds", insert --as S,S,S-stereoisomers--.

Claim 7, Col. 8, lines 30-34, delete "$\phi\text{-}\overset{\overset{O}{\|}}{C}\text{-}CH\text{=}\overset{\overset{COOH}{|}}{C}H$" and insert, therefore, --$R\text{-}\overset{\overset{O}{\|}}{C}\text{-}CH\text{=}\overset{\overset{CO_2R_1}{|}}{C}H$--.

Claim 7, Col. 8, line 37, "said ester to otain the diprotected" should read --said ester with hydrogen to obtain the desired--.

UNITED STATES PATENT AND TRADEMARK OFFICE
CERTIFICATE OF CORRECTION

PATENT NO. : 4,442,030

DATED : April 10, 1984

INVENTOR(S) : W. J. Greenlee

It is certified that error appears in the above-identified patent and that said Letters Patent is hereby corrected as shown below:

Claim 7, Col. 8, line 38, after "ester" insert --of Formula I--.

Claim 7, Col. 8, line 38, after "and," insert --optionally--.

Claim 7, Col. 8, line 38, delete "diprotected" and insert, therefore, --desired--.

Signed and Sealed this

Twenty-fifth Day of July, 1989

Attest:

DONALD J. QUIGG

Attesting Officer

Commissioner of Patents and Trademarks